United States Patent
Wouters et al.

(10) Patent No.: US 11,040,120 B2
(45) Date of Patent: *Jun. 22, 2021

(54) KIT FOR RADIOLABELLING WITH 68GA COMPRISING A METAL INHIBITOR

(71) Applicant: ANMI S.A., Liége (BE)

(72) Inventors: Ludovic Wouters, Herve (BE); Geoffroy Kaisin, Seraing (BE); André Luxen, Ocquier-Clavier (BE); Marc Léonard, Flémalle (BE); Samuel Voccia, Liége (BE)

(73) Assignee: ANMI S.A., Liége (BE)

( * ) Notice: Subject to any disclaimer, the term of this patent is extended or adjusted under 35 U.S.C. 154(b) by 46 days.

This patent is subject to a terminal disclaimer.

(21) Appl. No.: 15/505,941

(22) PCT Filed: Jul. 28, 2015

(86) PCT No.: PCT/EP2015/067211
§ 371 (c)(1),
(2) Date: Feb. 23, 2017

(87) PCT Pub. No.: WO2016/030103
PCT Pub. Date: Mar. 3, 2016

(65) Prior Publication Data
US 2018/0230068 A1 Aug. 16, 2018

(30) Foreign Application Priority Data
Aug. 29, 2014 (BE) .................................. 2014/0653

(51) Int. Cl.
*A61K 51/04* (2006.01)
*C07B 59/00* (2006.01)

(52) U.S. Cl.
CPC ........ *A61K 51/0482* (2013.01); *C07B 59/008* (2013.01); *C07B 2200/05* (2013.01)

(58) Field of Classification Search
None
See application file for complete search history.

(56) References Cited

U.S. PATENT DOCUMENTS

| 4,387,303 | A | 6/1983 | Benjamins | |
|---|---|---|---|---|
| 7,230,085 | B2 * | 6/2007 | Griffiths | A61K 47/6849 530/387.3 |
| 8,007,766 | B2 | 8/2011 | Velikyan et al. | |
| 2003/0176784 | A1 | 9/2003 | Griffiths et al. | |
| 2006/0182687 | A1 | 8/2006 | Yang et al. | |
| 2007/0269375 | A1 | 11/2007 | Chen et al. | |
| 2012/0009124 | A1 | 1/2012 | Port et al. | |
| 2012/0134920 | A1 | 5/2012 | D'Souza et al. | |
| 2013/0130537 | A1 | 5/2013 | Keswani | |
| 2013/0310537 | A1 | 11/2013 | Mueller | |
| 2014/0171637 | A1 | 6/2014 | Fungazza et al. | |
| 2018/0230069 | A1 | 8/2018 | Wouters et al. | |
| 2018/0267050 | A1 | 9/2018 | Wouters et al. | |
| 2019/0361030 | A1 | 11/2019 | Wouters et al. | |

FOREIGN PATENT DOCUMENTS

| JP | 2009-161549 | A | 7/2009 |
|---|---|---|---|
| RU | 2333557 | C2 | 9/2008 |
| WO | 03/059397 | A2 | 7/2003 |
| WO | 2008119036 | A2 | 10/2008 |
| WO | 2010092114 | A1 | 8/2010 |
| WO | 2010141833 | A2 | 12/2010 |
| WO | 2013/024013 | A2 | 2/2013 |
| WO | 2013024013 | A2 | 2/2013 |
| WO | 2014066733 | A2 | 5/2014 |
| WO | 2016/030104 | A1 | 3/2016 |
| WO | 2016030103 | A1 | 3/2016 |
| WO | 2017191604 | A2 | 11/2017 |

OTHER PUBLICATIONS

PCT International Search Report and Written Opinion dated Nov. 12, 2015 for PCT International Patent Application No. PCT/EP2015/067211, 12 pages.
Search Report dated Jan. 26, 2015 for Belgian Patent Application No. 2014/0653, 13 pages.
Maus S et al., entitled "Aspects on radiolabeling of 177Lu-DOTA-TATE: After C18 purification re-addition of ascorbic acid is required to maintain radiochemical purity," International Journal of Diagnostic Imaging, 2014, vol. 1, No. 1, pp. 5-12.
Communication Pursuant to Article 94(3) EPC dated Nov. 20, 2018 in connection with European Patent Application No. 15748207.6, 8 pages.
Communication Pursuant to Article 94(3) EPC dated Nov. 20, 2018 in connection with European Patent Application No. 15748208.4, 7 pages.
Haubner, Roland et al: "Development of 68Ga-labelled DTPA galactosyl human serum albumin for liver function imaging", European Journal of Nuclear Medicine and Molecular Imaging, vol. 40, No. 8, Apr. 12, 2013, pp. 1245-1255.
Prinsen, Kristof et al: "Development and evaluation of a 68Ga labeled pamoic acid derivative for in vivo visualization of necrosis using positron emission tomography", Bioorganic & Medicinal Chemistry, vol. 18, No. 14, Jul. 15, 2010, pp. 5274-5281.
Koop, Bernd et al: "Labelling of a monoclonal antibody with 68Ga using three DTPA-based bifunctional ligands and their in vitro evaluation for application in radioimmunotherapy", Radiochimica Acta, vol. 95, No. 1, Jan. 1, 2007, pp. 39-42.
Choi, Jae Yeon et al: "Development of Ga-labeled mannosylated human serum albumin (MSA) as a lymph node imaging agent for positron emission tomography", Nuclear Medicine and Biology, vol. 38, No. 3, Sep. 29, 2010, pp. 371-379.
Prata, M. I. M. et al: "Targeting of lanthanide(III) chelates of DOTA-type glycoconjugates to the hepatic asyaloglycoprotein receptor: cell internalization and animal imaging studies", Contrast Media & Molecular Imaging, vol. 1, No. 6, Jan. 1, 2006, pp. 246-258.

(Continued)

*Primary Examiner* — Jennifer Lamberski
(74) *Attorney, Agent, or Firm* — Amster, Rothstein & Ebenstein LLP

(57) ABSTRACT

The present invention relates to a kit for radiolabelling a targeting agent with gallium-68. The present invention also relates to the use of the kit for radiolabelling a targeting agent, a method for radiolabelling a targeting agent with gallium-68 using the kit, and a method of preparation of the kit.

11 Claims, No Drawings

(56) References Cited

OTHER PUBLICATIONS

Japanese Notification of Reasons for Refusal issued in Application No. 2017-530410, dated Feb. 5, 2019.
Larenkov A. A. et al., "Gallium Radionuclides in Nuclear Medicine: Radiopharmaceuticals Based on 68Ga," Medical radiology and radiation safety, 2011, vol. 56, No. 5, 56-73.
Russian Search Report dated Dec. 19, 2018 in connection with Russian Application No. 2017109582.
Russian Office Action, Dec. 2018, in connection with Russian Application No. 2017109582.
Eppard E et al., entitled "Ethanol-Based Post-processing of Generator-Derived 68Ga Toward Kit-Type Preparation of 68GA-Radiopharmaceuticals," Journal of Nuclear Medicine, vol. 55, No. 6, Jun. 2014, pp. 1023-1028.
Office Action dated Nov. 8, 2019 from Russian Patent Application No. 2017109583.
Green et al., "Carbohydrate-Bearing 3-Hydroxy-4-pyridinonato Complexes of Gallium(III) and Indium(III)," Bioconjugate Chem., vol. 16, No. 6, 2005, pp. 1597-1609.
Rizzello et al., "Synthesis and Quality Control of 68GA Citrate for Routine Clinical PET," Nuclear Medicine Communications, vol. 30, No. 7, 2009, pp. 542-545.
Third Party Submission Under 37 CFR § 1.290 dated Mar. 18, 2019 in U.S. Appl. No. 15/981,951.
International Search Report and Written Opinion dated Nov. 13, 2015 in PCT International Appln. No. PCT/EP2015/067213.
Russian Office Action dated Nov. 8, 2019 in Russian Application No. 2017109582 with English language translation.
Cerchiaro et al., "Investigations of Different Carbohydrate Anomers in Copper(II) Complexes With D-Glucose, D-Fructose, and D-Galactose by Raman and EPR Spectroscopy," Carbohydrate Research, vol. 340, Aug. 25, 2005, pp. 2352-2359.
Norkus, "Metal Ion Complexes With Native Cyclodextrins. An Overview," J. Incl. Phenom. Macrocycl. Chem., vol. 65, Apr. 30, 2009, pp. 237-248.
Mexican Office Action dated Oct. 27, 2020 from Mexican Patent Appln. No. MX/a/2017/002361 (with English language translation attached).
Leyva Ramos et al., "Agentes Quelantes Bifuncionales Utilizados en la Síntesis de Radiofármacos," Rev. Mex. Cienc. Farm., vol. 44, No. 1, Jan.-Mar. 2013, pp. 7-23 (with English language Abstract and concise explanation included in Office Action—see description of reference No. D5).
Australian Examination Report dated Dec. 2, 2019 for Australian Patent Appl. No. 2015309188.
Price E.W. and Orvig C. Matching chelators to radiometals for radiopharmaceuticals. Chemical Society Reviews, vol. 43, No. 1, Jan. 7, 2014, pp. 260-290.

* cited by examiner

KIT FOR RADIOLABELLING WITH 68GA COMPRISING A METAL INHIBITOR

CROSS-REFERENCE TO RELATED APPLICATIONS

This application is a U.S. national stage entry under 35 U.S.C. § 371 of PCT International Patent Application No. PCT/EP2015/067211, filed Jul. 28, 2015, which claims priority to Belgian Patent Application No. 2014/0653, filed Aug. 29, 2014, the contents of which are incorporated herein by reference in their entirety.

TECHNICAL FIELD

The present invention is related to kit for radiolabelling

BACKGROUND

Recently, some very interesting clinical results based on gallium-68 radiolabeled molecules for imaging in vivo by PET were published and presented. These radiotracers are generally made by assembly of a chelating agent with a targeting agent, generally DOTA-functionalized targeting agents, allowing, respectively, the reaction with a metallic radioisotope or radiometal and biological/metabolic activity of the radiotracer. However, due to the short half-life of gallium-68 (68 minutes), the radiotracer, i.e. radiolabelled chelate-functionalized targeting agent, based on this radioisotope are not suitable for long-distance distribution and require on the spot production and suitable production equipment, such as automated synthesizers, for the radiolabelling process, making it difficult for widespread use in routine nuclear medicine.

The labelling reaction with the gallium-68 is performed by chelating the radioactive metal with a suitable chelating agent in a suitable reaction medium, usually in a buffered medium in order to ensure an optimum pH for both the chelation reaction and the gallium solubility.

Gallium-68 itself is obtained from a generator. Said generator is an alternative to the in situ production using a cyclotron or daily delivery of radioisotopes. The system was initially developed for technecium-99. The principle is based on the radiochemical separation between a parent element of long half-life (or nonradioactive elements such as germanium-68) contained in the generator and a daughter element which is a short half-life element resulting from the disintegration of the parent element. The daughter is recovered with excellent radiochemical purity and radionuclidic properties (i.e. without contamination from other radionuclides or other radiochemical impurities) and with good chemical purity (low metal ion content). This separation is made possible by the different chemical properties of the two elements (parent and daughter).

The characteristics of a germanium-68/gallium-68 generator can be summarized as follows:

The eluate is obtained in an acid solution (0.05M-5M HCl, specified by the manufacturer of the generator)

The eluate contains zinc-68, resulting from both the manufacturing process of germanium-68 and disintegration of gallium-68, whose concentration increases continuously in function of time elapsed since the last elution of the generator. Indeed, this zinc-68 accumulates in the generator. This can be detrimental to the performance of radiolabelling since this zinc-68 enters in direct competition with gallium-68 for chelation reactions used for radiolabelling.

The eluate further contains germanium-68 (the "breakthrough") released from the generator.

The eluate also contains a variety of metal leaching from the solid phase of the generator column, tubings, but also brought by the HCl used for elution:

Microg/ml level: Fe (III), Zn (II), Al (III)

Picog/L level: Mn (II), Pb (II), Ti (IV), Cr (III), Ni (II) (Sn (IV))

The efficiency of the chelation reaction is dependent on a suitable pH, but also on possible competition of the metallic impurities mentioned above with the gallium-68 during the chelation reaction as well. In addition, it is generally accepted that heat facilitates the chelation reaction for the most commonly used gallium-68 based radiotracers.

In the state of the art, the presence of metal ions that compete with gallium-68 is generally reduced by pre-labelling purification or fractionation of the eluate (as described in WO 2010/092114). These additional steps however represent a loss of radioactivity resulting from, either wasted time or the process itself. These losses can reach up to 30% of the total radioactivity, respectively, 10% due to decay and 20% coming from the pre-purification process itself.

The possibility of partial chelation of gallium-68 requires, in general, a final post-labelling purification in order to obtain a radiotracer having a radiochemical purity that meets the pharmaceutical specifications (>90% radiochemical purity). These steps also represent an additional loss of activity that can rise to up to 10% resulting from wasted time or the process itself.

According to known processes, at the end of the radiolabelling, a sequestering agent having a particular affinity for the gallium-68 may be added to chelate the non-reacted part of the isotope. This complex formed by the sequestering agent and the non-reacted gallium-68 is then discarded in order to reach a better radiochemical purity after radiolabelling.

In addition, the need for these pre- and post-labelling purification steps makes these gallium-68 labeled radiotracer synthesis dependent, to some extent, on automation and on the use of a synthesis module. In addition to technical expertise, this requires extra time loss unfavorable to the overall performance.

Due to the short half-life of the radionuclide (68 minutes) and to limited activity supplied by the generator (max. 100 mCi), any improvement in order to achieve rapid, direct and high efficiency chelation of target molecules is thus highly desirable.

In order to maintain the pH of the labelling solution in a range where it is possible to ensure both the chelating reaction and the gallium-68 solubility, a buffering medium is generally used. The desired buffer must be nontoxic, must effectively maintain the pH within a range of 3.0 to 5.0, should not compete with gallium-68 ions and have preferably a low capacity for metal chelation with regard to the capacity of the chelating agent as assembled with the targeting agent. It must also be able to tolerate possible small changes in the volume of generator eluate (and therefore the amount of HCl), i.e. it must be strong enough to maintain the pH within the desired range with 10% changes in the volume of eluate.

Management of competing metal impurities is another challenge. It has been shown in WO2013024013 that adding a co-chelating agent could allow inhibition of competing metal impurities. Indeed, any species that would inhibit metal impurities by avoiding or having limited capacity to interfere negatively on the gallium-68 chelation reaction can act as a trap for these impurities. In other words, this inhibitory effect brings the apparent concentration of competitor metal, i.e. the concentration of metallic impurities yet available for chelation to a level which allows high yields and reproducible radiolabelling. This co-chelating agent is by definition different than the chelating agent assembled with the targeting agent.

In this context, it is clear that a need exists for an improved process for the preparation of $^{68}$Ga complex which overcomes one or more of the above mentioned problems. This involves identifying an appropriate medium that maintains the pH within a tolerable range, to handle the metal contamination, which avoids the need to heat for promoting the chelating reaction and allows gallium-68 chelation yields upper 90%.

SUMMARY OF THE INVENTION

The present invention relates to the following aspects:
Aspect 1. A radiolabelling kit comprising:
  a suitable amount of acetate salt or buffer to balance at least the acidic pH eluate from a gallium-68 generator to a pH value ranging from 3 to 5 when said generator is eluted in the kit;
  a chelate-functionalized targeting agent, said chelate function being able to chelate gallium-68 in the radiolabelling conditions; and
  a metal inhibitor, which is a co-chelating agent, capable of inactivating contaminating metals other than gallium-68 without interfering with the chelation between gallium-68 and said chelate-functionalized targeting agent, under the conditions of the labelling reaction.

Aspect 2. The kit according to aspect 1, wherein said acetate salt, chelate-functionalized targeting agent and metal inhibitor are (co-)lyophilized.

Aspect 3. The kit according to aspect 1, wherein said chelate-functionalized targeting agent and metal inhibitor are (co-)lyophilized, and wherein said acetate salt or buffer is present separately and can be added subsequently.

Aspect 4. The kit according to aspect 1, wherein said chelate-functionalized targeting agent and metal inhibitor are (co-)lyophilized, an acetate buffer being added subsequently.

Aspect 5. The kit according to anyone of aspects 1 to 4, wherein the acetate salt or acetate salt buffer comprises a quantity of acetate salt adjusted to the type of the gallium-68 generator used.

Aspect 6. The kit according to anyone of aspects 1 to 4, wherein the acetate salt or acetate salt buffer is present in a fixed concentration to balance the acidic pH eluate from a gallium-68 generator to a pH value ranging from 3 to 5 when said generator is eluted in the kit after addition of HCL to the kit.

Aspect 7. The kit according to anyone of aspects 1 to 6, wherein the chelate functional group of the targeting agent is capable of forming a stable complex with Ga3+.

Aspect 8. The kit according to anyone of aspects 1 to 7, wherein the chelate functional group of the targeting agent is selected from the group comprising: NOTA and derivatives, Tris(hydroxypyridinone) (THP) and derivatives, open-chain chelators such as HBED, MPO, EDTA, 6SS, B6SS, PLED, TAME, and YM103; NTP (PRHP) 3, H2dedpa and its derivatives, (4,6-MeO2sal) 2-BAPEN, and citrate and its derivatives.

Aspect 9. The kit according to anyone of aspects 1 to 8, wherein the acetate salt is present in an of amount between 5 mg and 1000 mg, preferably in an amount of between 10 mg and 750 mg, more preferably in an amount of between 20 mg and 500 mg.

Aspect 10. The kit according to anyone of aspects 1 to 9, wherein the metal inhibitor is present in a micromolar quantity, preferably in a nanomolar quantity, more preferably in a quantity of below 500 nanomoles, even more preferably in a quantity of below 100 nanomoles.

Aspect 11. The kit according to anyone of aspects 1 to 10, wherein said metal inhibitor is selected from the group comprising: DOTA and its derivatives, DTPA and its derivatives, and sugars.

Aspect 12. The kit according to anyone of aspects 1 to 11, wherein said metal inhibitor is selected from the group comprising: monosaccharides and their derivatives, disaccharides and their derivatives, and polysaccharides and their derivatives.

Aspect 13. The kit according to anyone of aspects 1 to 12, wherein said metal inhibitor and said functionalised agent are chemically linked.

Aspect 14. The kit according to anyone of aspects 1 to 13, wherein said metal inhibitor and said functionalised agent are chemically linked, through a linker that is unstable in the radiolabelling conditions.

Aspect 15. Use of the kit according to anyone of aspects 1 to 14, for radiolabelling a chelate-functionalized targeting agent with gallium-68 carried out at a temperature near or equal to room temperature.

Aspect 16. A method for radiolabelling a chelate-functionalized targeting agent with gallium-68, comprising the elution of a gallium-68 generator with an eluent comprising an acid, in a kit according to anyone of aspects 1 to 13.

Aspect 17. The method according to aspect 16, wherein the acid is HCl.

Aspect 18. The method according to aspect 16 or 17, comprising additionally the step of adding HCl to the kit before elution.

Aspect 19. The method according to anyone of aspects 16 to 18, wherein the radiolabelling is performed at a pH comprised between 3 and 5, preferably between 3,5 and 4,5, more preferably between 3,9 and 4,3.

Aspect 20. The method according to anyone of aspects 16 to 19, wherein the radiolableing reaction is carried out at a temperature of below 50° C., preferably of ambient or room temperature (e.g. of between 20 and 30° C.).

Aspect 21. A solution obtainable by elution of a gallium-68 generator with an eluent comprising an acid, in a kit according to anyone of aspects 1 to 14.

Aspect 22. A solution obtainable by elution of a gallium-68 generator with an eluent comprising a base, in a kit according to anyone of aspects 1 to 14.

Aspect 23. A solution obtainable by elution of a gallium-68 generator with an eluent that is concentrated or purified prior to its transfer in a kit according to anyone of aspects 1 to 14.

Aspect 24. The solution according to anyone of aspects 21 to 23, having a pH of between 3 and 5, preferably between 3,5 and 4,5, more preferably between 3,9 and 4,3.

Aspect 25. A process for preparing a radiolabelling kit according to anyone of aspects 1 to 14, comprising the steps of:
a) preparing or providing a solution comprising suitable amount of acetate salt or buffer to balance at least the acidic pH eluate from a gallium-68 generator to a pH value ranging from 3 to 5, preparing or providing a chelate-functionalized targeting agent and preparing or providing an inhibitor of metal; and
b) lyophilizing the solution obtained in step a).

Aspect 26. A process for preparing a radiolabelling kit according to anyone of aspects 1 to 14, comprising the steps of:
a) preparing or providing a solution comprising a chelate-functionalized targeting agent and an inhibitor of metal;
b) lyophilizing the solution obtained in step a), and
c) adding the acetate salt as a powder in the obtained lyophilized product in step b).

Aspect 27. A process for preparing a kit according to anyone of aspects 1 to 14, comprising the steps of:
a) preparing a solution comprising a chelate-functionalized targeting agent and an inhibitor of metal;
b) lyophilizing the solution obtained in step a), and
c) adding an acetate buffer in the obtained lyophilized product in step b).

Aspect 28. The invention further provides a process for preparing a kit according to anyone of aspects 1 to 14, comprising the steps of:
a) preparing a solution comprising the acetate salt, a chelate-functionalized targeting agent and an inhibitor of metal; and
b) optionally freeze the solution obtained in step a).

Aspect 29. A process for radiolabelling a target agent with gallium-68, wherein a metal inhibitor is included either in the eluate of the gallium-68 generator, or in the HCl solution added before elution of the gallium-68 generator, wherein said metal inhibitor is present in the radiolabelling solution.

DETAILED DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

In the following passages, different aspects or embodiments of the invention are defined in more detail. Every aspect or embodiment so defined may be combined with each of the other aspects or embodiments unless stated otherwise. In particular, any feature indicated as being preferred or advantageous in one embodiment may be combined with any other embodiment or embodiments indicated as being preferred or advantageous.

The present invention overcomes one or more of the problems identified and observed in the state of the art and allows the direct radiolabelling of a chelate-functionalized targeting agent with gallium-68 at a temperature below 50° C. and preferably at room temperature, using a kit as described herein, this gallium-68 being eluted from a germanium-68/gallium-68 generator in an acidic aqueous solution.

Accordingly, in one aspect, the invention provides a kit comprising:

A suitable amount of acetate salt to balance at least the acidic pH eluate from a gallium-68 generator to a pH value ranging from 3 to 5 when said generator is eluted in the kit; and A chelate-functionalized targeting agent, able to chelate gallium-68 in the radiolabeling conditions A metal inhibitor, which is a co-chelating agent, capable of inactivating metals other than gallium-68 without interfering with the chelation between gallium-68 and the said chelate-functionalized targeting agent, under the conditions of the labelling reaction. In other words, said metal inhibitor is selected for its ability to chelate contaminating metals interfering and competing with the chelation of gallium-68 while being mostly unable gallium-68 in the said conditions of the labelling reaction as opposed to the chelate-functionalized targeting agent.

Said kit being suitable to perform the radiolabelling reaction of said chelate-functionalized targeting agent with gallium-68 as carried out at a temperature near or equal to room temperature, preferably at a temperature below 50° C. and more preferably at room temperature.

The invention also relates to a kit wherein the acetate salt, the chelate-functionalized targeting agent and the metal inhibitor are (co-) lyophilized.

The invention also relates to a kit wherein the chelate-functionalized targeting agent and the metal inhibitor are (co-)lyophilized, the acetate salt being added subsequently.

The invention also relates to a kit wherein the chelate-functionalized targeting agent and the metal inhibitor are (co-)lyophilized, an acetate buffer being added subsequently.

The invention also relates to a kit wherein the acetate salt, the chelate-functionalized targeting agent and the metal inhibitor are solubilized and further frozen.

The kit as described herein can not only provide an optimum pH for carrying out the chelation reaction or radiolabelling, but also allows to tolerate or manage the variation of the eluate volume and acidity associated with different types of gallium-68 generators, through the use of a suitable amount of acetate salt that when mixed with the acid generator eluate, form an acetic acid/acetate buffer having an acid pH comprised in the interval 3-5. In these conditions, the amount of non-chelated gallium-68 because of a too low or too high pH, which leads respectively to a high content of free gallium-68 cations or to gallium-68 hydroxides (gallium colloids), is minimized.

In addition, the acetate buffer is well tolerated as a buffer or as an excipient for pharmaceuticals.

Furthermore, the present inventors have found that a metal inhibitor can be used in the radiolabelling method for neutralizing, at least partially, interfering species and allows the gallium-68 to react with the chelate-functionalized targeting agent. These metal inhibitors may temporarily or permanently remove metals that compete with gallium-68 for the reaction with the chelate-functionalized targeting agent. Said metal inhibitor is thus unable to chelate gallium-68 in the said conditions of the labelling reaction, but chelate other metals interfering with the chelation of gallium-68 by the chelate-functionalized targeting agent. The presence of a metal inhibitor during the radiolabelling reaction provides an advantageous alternative to current approaches for managing the presence of metallic impurities, such as increasing the amount chelate-functionalized targeting agent, or the pre-treatment of the eluate of the generator, since these additional purification steps consume time (and radioactivity).

These aspects as described herein advantageously allow obtaining an appropriate chelation yield, particularly of about 90% and more, and therefore a sufficient radiochemical purity without any preliminary or further final purification.

The presence of a chelate-functionalized targeting agent, an acetate salt and a metal inhibitor in the kit advantageously allows to directly elute gallium-68 generator in the kit and performing the radiolabelling reaction without the need for any prior or subsequent operation.

In addition, all kit components as described herein can be lyophilized altogether or frozen which ensures a longer shelf life.

Thus, the main advantages of a kit as disclosed herein that differentiate said kit from the state of the art are:
  A completely dry or frozen kit that allows a better shelf life of the chelate-functionalized targeting agent;
  The possibility of radiolabelling without the need for an automated synthesizer;
  The possibility of a radiolabelling without the need for heating;
  The presence of a metal inhibitor which advantageously allows to use less chelate-functionalized targeting agent and allowing the implementation of more affordable radiopharmaceutical synthesis;
  The presence of a metal inhibitor which advantageously allows to improve the radiolabelling yields;
  The fact that any brand generator can be used with this kit provided as acetate or partially neutralized with HCl so that when mixed with the acid generator eluate, the optimal pH for the radiolabelling is obtained.

As used herein, "acetate" refers to the anionic molecule $CH_3COO-$. The term "acetate salt" herein is meant any metal salt acetate. Non-limiting examples of acetate salts include sodium acetate, potassium acetate, aluminium acetate, and ammonium acetate. Preferably sodium acetate is used in the kits as described herein. Said acetate salt can be present in solid form or can be comprised in a buffered solution or buffer.

The amount of salt of the acetate present in the kit as described herein can be adapted according to the type and/or the kind of gallium-68 generator, in particular the quantity of acetate salt present in the kit is able to balance the pH, i.e. to manage the quantity of HCl as eluted from a gallium-68 generator such that the resulting solution has a pH between 3 and 5, preferably between 3.5 and 4.7, preferably between 3.9 and 4.5.

Alternatively, the kit as described in the present invention may comprise a fixed quantity of acetate salt. The amount of HCl differences from the generator eluate (depending on the type and/or the generator brand gallium-68) can then be adjusted by adding an appropriate amount of HCl to the kit as described herein prior to elution. The amount of HCl added to the kit as described in the present invention is partially neutralizing the acetate salt such that the non-neutralized acetate salt is able to balance the pH of a quantity of HCl from a generator eluate such that the resulting solution has a pH between 3 and 5, preferably between 3.5 and 4.7, preferably between 3.9 and 4.5.

Preferably, the acetate salt is present in the kit as taught herein in an amount between about 1 mg and about 1000 mg, preferably in an amount between about 10 mg and about 750 mg, more preferably in an amount between about 20 mg and about 500 mg.

Metal inhibitors used in the present invention are selected for their ability to inhibit the competing metals, without (substantially) inhibiting gallium-68 ions in their chelation reaction with the chelate-functionalized targeting agent. Indeed, these metal inhibitors should (substantially) not interfere negatively on the main radiolabelling reaction or lead to the formation of secondary radiolabeled species. In other words metal inhibitors should have a limited or no capacity to complex gallium-68 in the conditions used for the radiolabelling reaction, i.e. below 50° C. in an acetate buffer between pH 3 and pH 5. Limited means at least 100 times less than the chelating agent used for the chelate-functionalized targeting agent.

It is interesting to note that the function of metal inhibitors in the present invention is the opposite of the function of the sequestering agents used in the prior art. Indeed, according to known methods, at the end of the labelling reaction, a sequestering agent having a particular affinity for the gallium-68 may be added to chelate the unreacted portion of the isotope, whereas, according to the present invention an agent capable of reducing the competition of metallic impurities other than the gallium-68 is added at the beginning of the reaction.

In addition, being able to perform the radiolabelling reaction at a temperature close to room temperature (<50° C.) advantageously allows the use of metal inhibitors that would not be usable at the usual temperatures of radiolabelling DOTA-functionalized targeting agents by such as used in WO2013024013, because they would be entering in direct competition with gallium-68 at such temperatures of above 50° C. The temperature is therefore also described in the invention as a parameter for adjusting the reactivity of the metal inhibitor.

As used herein, a "metal inhibitor" refers to any molecule capable of interacting with, or competing metals, or the chelating moiety of the chelate-functionalized targeting agent or with gallium-68 directly, to inhibit wholly or partially the chelation the chelate-functionalized targeting agent said competing metals and/or promote the chelating of gallium-68 by said targeting agent. Such metal inhibitors should have a limited or no capacity to complex gallium-68 in the conditions used for the radiolabelling reaction, i.e. below 50° C. in an acetate buffer between pH 3 and pH 5. Limited means at least 100 times less than the chelating agent used for the chelate-functionalized targeting agent.

Metal inhibitors are preferably selected from the group comprising or consisting of: DOTA and its derivatives, such as, DOTATOC, DOTANOC, DOTATA, TRITA, DO3A-Nprop, BisDO3A and TrisDO3A; DTPA and its derivatives such as tetra-tBu-DTPA, p-SCN-Bz-DTPA, MX-DTPA and CHX-DTPA; and sugars. Sugars used as metal inhibitors in the kit of the invention can be monosaccharides or derivatives of monosaccharides such as tetracetose, pentacetose, hexacétose, tetrose, pentose, hexose, D-mannose, D-fructose, and derivatives; and/or disaccharides and their derivatives such as maltose and its derivatives; and/or polysaccharides and their derivatives such as dextrins, cyclodextrins, cellulose and derivatives thereof.

Preferably, the metal inhibitor is present in the kit as described herein in micromolar amounts, preferably in nanomolar quantities, preferably in an amount of less than 500 nanomolar, still more preferably in an amount less than 100 nanomoles.

It is important to note that metal inhibitors as shown above can also be advantageously used in chelation reactions wherein other buffers than buffered acetic acid/acetate are used.

Metal inhibitors as shown above can also be advantageously used in chelation reactions wherein said metal inhibitor is included in the eluent generator, in the HCl solution, or in water possibly added before elution of the generator. Said metal inhibitor is thus found in the radiolabelling solution. The metal inhibitor may also be chemically bound to the chelate-functionalized targeting agent. This chemical bond can or cannot be a labile bond under the conditions of radiolabelling with the chelate-functionalized targeting agent. This means that in the conditions of radiolabelling the metal inhibitor is formed and released in situ. Examples of such preferred bonds are . . . .

As used herein, a "chelate-functionalized targeting agent" refers to a targeting agent capable of being labeled with a radioisotope such as for example gallium-68, by means of a chelating agent which is bound to the targeting molecule.

Preferred chelating agents for functionalizing a targeting agent to be radiolabeled with gallium-68 are those which form stable chelates with Ga3+, in particular 68-Ga3+(the radioisotope generator eluted from a germanium-68/gallium-68 generator using HCl), at least for a time sufficient for diagnostic investigations using such radiolabelled targeting agents. Suitable chelating agents include aliphatic amines, linear or macrocyclic such as macrocyclic amines with tertiary amines. While these examples of suitable chelating agents are not limited, they preferably include the NOTA and its derivatives, such as TACN, TACN-TM, DTAC, H3NOKA, NODASA, NODAGA, NOTP, NOTPME, PrP9, TRAP, Trappist Pr, NOPO, TETA; Tris (hydroxypyridinone) (THP) and derivatives, chelates open chain such as HBED, DFO or desferrioxamine or desferal, EDTA, 6SS, B6SS, PLED, TAME, YM103; NTP (PRHP) 3; the H2dedpa and its derivatives such as H2dedpa-1, 2-H2dedpa, H2dp-bb-NCS, and H2dp-N-NCS; (4,6-MeO2sal) 2-BAPEN; and citrate and derivatives thereof.

The chelate-functionalized targeting agent can be a peptide, for example, a peptide comprising 2 to 20 amino acids, a polypeptide, a protein, a vitamin, a saccharide, for example a monosaccharide or a polysaccharide, an antibody and its derivatives such as nanobodies, diabodies, antibodies fragments, nucleic acid, an aptamer, an antisense oligonucleotide, an organic molecule, or any other biomolecule that is able to bind to a certain diagnostic target or to express a certain metabolic activity.

Chelate-functionalized targeting agents as described herein preferably have a capacity of biological targeting. Non-limiting examples of suitable targeting agents include molecules that target VEGF receptors, analogs of bombesin or GRP receptor targeting molecules, molecules targeting somatostatin receptors, RGD peptides or molecules targeting $\alpha v\beta 3$ and $\alpha v\beta 5$, annexin V or molecules targeting the apoptotic process, molecules targeting estrogen receptors, biomolecules targeting the plaque . . . . More generally, a list of targeting molecules, organic or not, functionalized by a chelating agent can be found in the journal of Velikyan et al., Theranostic 2014, Vol. 4, Issue 1 "Prospective of 68Ga-Radiopharmaceutical Development."

In some embodiments, the metal inhibitor is included in the eluent generator, in the HCl solution, or possibly in the added water prior to elution of the generator. Said metal inhibitor and is thus found in the radiolabelling solution.

The various components of the kit as described herein are preferably present in a container or vial, preferably a siliconized glass vial. However, also a kit wherein the individual components are present in separate containers or vials is envisaged.

The invention further provides a method for radiolabelling a targeting agent with gallium-68, said method comprising the elution of a gallium-68 generator with an eluent comprising an acid, in a kit as described herein, e.g. comprising the metal inhibitor, the chelate-functionalized targeting agent and acetate salt.

As indicated above, when the chelate-functionalized targeting agent is included in the kit, a gallium-68 generator can be eluted directly into the kit. In other embodiments, the chelate-functionalized targeting agent can be added to a kit comprising the acetate salt and a metal-inhibiting agent as described herein, prior to elution.

In some embodiments, the gallium-68 generator is eluted directly into the kit. In other embodiments, water is added to the solution prior to elution.

In some embodiments of the present invention, an appropriate amount of HCl is added to the solution prior to elution. Said HCl is added to partially neutralize the acetate. The amount of HCl added, preferably partially neutralizes the quantity of acetate salt in such a manner that the remaining quantity of acetate salt, i.e. unneutralized acetate salt, is able to balance the pH of said amount of HCl from the generator eluate (and thus dedicated to one type or brand of given generator) such that the pH of the solution obtained for the radiolabelling reaction or chelating reaction, resulting from the addition of HCl and the generator eluate in the kit as described herein, is in a pH range between 3 and 5, preferably between 3.5 and 4.5, preferably between 3.9 and 4.3. Said HCl may be added directly to the solution, or after a certain amount of water is added to said kit.

All gallium-68 generator may be used in the methods of the present invention. Typically, a commercial gallium-68 generator comprises a column on which the germanium-68 is fixed. A gallium-68 generator is typically eluted with an eluent comprising an acid, preferably HCl. Therefore, in preferred embodiments of the method, as taught herein, the gallium-68 generator is eluted with an eluent comprising HCl.

After elution of the gallium-68 generator in the kit as described herein, the solution obtained is left to react in the radiolabelling reaction for a short period of time, in particular between about 2 minutes and about 60 minutes, preferably from about 2 minutes to about 30 minutes, for example about 10 minutes.

Preferably, the radiolabelling reaction or chelation is performed at a temperature below 50° C., preferably of below 45° C., below 40° C., below 35° C., or below 30° C., most preferably at room temperature, e.g. between 20 and 25° C.

Preferably, the radiolabelling reaction or chelation is performed at a pH between about 3 and about 5, more preferably between about 3.5 and about 4.5, more preferably between about 3.9 and about 4.3.

The invention also encompasses the solution obtained by elution of a gallium-68 generator with an eluent comprising an acid, preferably HCl, in a kit as taught herein.

Preferably, said solution has a pH between about 3 and about 5, preferably between about 3.5 and about 4.5, more preferably between about 3.9 and about 4.3.

The invention also discloses a gallium-68 radiolabeled targeting agent, obtained by anyone of the methods as described herein.

In one aspect, the invention also provides a preparation method of a kit as described herein, said method comprising the steps of:
a) preparing a solution comprising the acetate salt, a chelate-functionalized targeting agent and an inhibitor of metal; and
b) lyophilizing the solution obtained in step a).

Alternatively, the invention further provides a process for preparing a kit of the invention comprising the steps of:
a) preparing a solution comprising a chelate-functionalized targeting agent and an inhibitor of metal; and
b) lyophilizing the solution obtained in step a).
c) adding the acetate salt as a powder in the obtained lyophilized product in step b).

Further alternatively, the invention further provides a process for preparing a kit of the invention comprising the steps of:
a) preparing a solution comprising a chelate-functionalized targeting agent and an inhibitor of metal; and
b) lyophilizing the solution obtained in step a).
c) adding an acetate buffer in the obtained lyophilized product in step b).

Finally, the invention further provides a process for preparing a kit of the invention comprising the steps of:
a) preparing a solution comprising the acetate salt, a chelate-functionalized targeting agent and an inhibitor of metal; and
b) optionally freeze the solution obtained in step a).

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The above aspects and embodiments are further supported by the following non-limiting examples.

EXAMPLES

Example 1: Generator E & Z/NODAGA Peptide without Metal Inhibitor

Labelling a Peptide with a 68Ga Eluate of 5 mL of 0.1 M HCl

A commercial gallium-68 generator 1850 MBq (Eckert & Ziegler) is eluted with 5 mL of 0.1M HCl (Ultrapure grade) directly into a flask containing 150 mg of sodium acetate (Ultrapure grade) lyophilized, 240 µl of HCl 3M (Ultrapure grade), 760 µl of Milli-Q and 50 µg lyophilized NODAGA-NOC. The flask was left for 10 min at room temperature. The product is obtained with a radiochemical purity of 64% according to TLC analysis of the reaction medium.

Example 2

Similarly to what was done in Example 1 different combinations were tested and are summarized in the table below:

| Entry | Acetate | Chelating agent use in the chelate-functionalized targeting agent | Inhibitor | Generator | Radiolabelling yield for 10 minutes, room T° vs radiolabelling yield without metal inhibitor using similar conditions | Generator cleaniliness | Kit Preparation* |
|---|---|---|---|---|---|---|---|
| 1 | 150 mg | NOTA 25 µg | DOTA | E&Z | 82% vs 51% | Generator cleaned | A |
| 2 | 150 mg | NOTA 25 µg | Fructose | E&Z | 87% vs 51% | Generator cleaned | A |
| 3 | 150 mg | NOTA 25 µg | Beta-cyclodextrin | E&Z | 83% vs 51% | Generator cleaned | A |
| 4 | 150 mg | NODAGA 25 µg | Beta-cyclodextrin | E&Z | 95% vs 64% | Generator cleaned | A |
| 5 | 150 mg | HBED 25 µg | Beta-cyclodextrin | E&Z | 91% vs 77% | Generator cleaned | A |
| 6 | 150 mg | HBED 25 µg | Fructose | E&Z | 94% vs 77% | Generator cleaned | A |
| 7 | 150 mg | NOTA 10 µg | Fructose | E&Z | 85% vs 39% | Generator cleaned | A |
| 9 | 150 mg | NODAGA 10 µg | Beta-cyclodextrin | E&Z | 84% vs 55% | Generator cleaned | A |
| 9 | 150 mg | HBED 10 µg | Beta-cyclodextrin | E&Z | 87% vs 51% | Generator cleaned | A |
| 10 | 150 mg | NODAGA 50 µg | Beta-cyclodextrin | ITG | 94% vs 46% | Generator cleaned | A |
| 11 | 150 mg | NODAGA 50 µg | Beta-cyclodextrin | E&Z | 97% vs 70% | Generator cleaned | A |
| 12 | 150 mg | NODAGA 50 µg | D-Mannose | E&Z | 91% vs 44% | Generator not cleaned | A |
| 13 | 150 mg | NODAGA 50 µg | DOTA | E&Z | 95% vs 70% | Generator cleaned | A |
| 14 | 150 mg | NODAGA 50 µg | Beta-cyclodextrin | iThemba | 91% vs 61% | Generator cleaned | A |
| 15 | 150 mg | NODAGA 50 µg | Fructose | E&Z | 95% vs 70% | Generator cleaned | A |
| 16 | 150 mg | HBED 20 µg | DOTA | ITG | 91% vs 75% | Generator cleaned | A |
| 17 | 150 mg | NODAGA 25 µg | D-Mannose | ITG | 95% vs 60% | Generator cleaned | A |

-continued

| Entry | Acetate | Chelating agent use in the chelate-functionalized targeting agent | Inhibitor | Generator | Radiolabelling yield for 10 minutes, room T° vs radiolabelling yield without metal inhibitor using similar conditions | Generator cleaniliness | Kit Preparation* |
|---|---|---|---|---|---|---|---|
| 18 | 150 mg | NODAGA 25 µg | Beta-cyclodextrin | ITG | 96% vs 60% | Generator cleaned | A |
| 19 | 150 mg | NODAGA 25 µg | tetra-tBu-DTPA | ITG | 89% vs 60% | Generator cleaned | A |
| 20 | 150 mg | NODAGA 25 µg | Beta-cyclodextrin | ITG | 96% vs 61% | Generator cleaned | B |
| 21 | 150 mg | NODAGA 25 µg | DOTA | E&Z | 94% vs 64% | Generator cleaned | B |
| 22 | 150 mg | NODAGA 25 µg | DOTA | E&Z | 89% vs 64% | Generator cleaned | C |
| 23 | 150 mg | NODAGA 25 µg | Glucose | ITG | 89% vs 61% | Generator cleaned | C |
| 24 | 150 mg | DFO 10 µg | DOTA | ITG | 98% vs 85% | Generator cleaned | A |

*
A = a preparation method comprising the steps of:
a) preparing a solution comprising the acetate salt, a chelate-functionalized targeting agent and an inhibitor of metal; and
b) lyophilizing the solution obtained in step a).
B = a preparation method comprising the steps of:
a) preparing a solution comprising a chelate-functionalized targeting agent and an inhibitor of metal; and
b) lyophilizing the solution obtained in step a).
c) adding the acetate salt as a solid
C = a preparation method comprising the steps of:
a) preparing a solution comprising a chelate-functionalized targeting agent and an inhibitor of metal; and
b) lyophilizing the solution obtained in step a).
c) adding the acetate salt as a buffer solution adapted to the generator used To conclude, the results above clearly show the increased gallium-68 radiolabelling yield of about 90% or more in all set-ups where a metal inhibitor as defined herein is used in addition to the chelator-functionalized targeting agent. If said agent is not added, much lower yields are obtained. The yield is virtually independent of the use of acetate in solid form or in buffer form. Also when the acetate salt is co-lyophilized with the metal inhibitor and the chelator-functionalized targeting agent, a very good yield is obtained.

The invention claimed is:
1. A radiolabelling kit comprising:
   a suitable amount of acetate salt or buffer to balance at least an acidic pH eluate from a gallium-68 generator to a pH value between 3 to 5 when said generator is eluted in the kit;
   a chelate-functionalized targeting agent, said chelate function being able to chelate gallium-68 in a radiolabelling reaction; and
   a metal inhibitor, which is a co-chelating agent, capable of inactivating contaminating metals without interfering with the chelation between gallium-68 and said chelate-functionalized targeting agent, under the conditions of said radiolabelling reaction,
      wherein said radiolabelling reaction is carried out at a temperature near or equal to room temperature and at a pH of between 3 and 5,
      wherein said chelate-functionalized targeting agent and said metal inhibitor are not chemically linked,
      wherein said metal inhibitor is selected from the group consisting of DOTA, DTPA, a monosaccharide and beta-cyclodextrin,
      wherein said targeting agent of the chelate-functionalized targeting agent is selected from the group consisting of a peptide, a peptide comprising 2 to 20 amino acids, a polypeptide, an antibody, a nanobody, a diabody, an antibody fragment, a nucleic acid, an aptamer, an antisense oligonucleotide, and an organic molecule, and
      wherein said chelate functional group of the chelate-functionalized targeting agent is selected from the group consisting of NOTA, NODAGA, Tris(hydroxypyridinone) (THP), HBED, DFO, 6SS, B6SS, PLED, YM103, and H$_2$dedpa.

2. The kit according to claim 1, wherein said acetate salt or buffer, chelate-functionalized targeting agent and metal inhibitor are lyophilized or co-lyophilized.

3. The kit according to claim 1, wherein said chelate-functionalized targeting agent and metal inhibitor are lyophilized or co-lyophilized, and wherein said acetate salt or buffer is present separately and can be added subsequently.

4. The kit according to claim 1, wherein the acetate salt or buffer comprises a quantity of acetate salt adjusted to the type of the gallium-68 generator used.

5. The kit according to claim 1, wherein the acetate salt or buffer is present in a fixed concentration to balance the acidic pH eluate from a gallium-68 generator to a pH value between 3 to 5 when said generator is eluted in the kit after addition of HCl to the kit.

6. The kit according to claim 1, wherein the acetate salt or buffer is present in an of amount between 5 mg and 1000 mg.

7. The kit according to claim 1, wherein the metal inhibitor is present in a micromolar quantity.

8. The radiolabelling kit according to claim 1, wherein the monosaccharide is glucose, fructose or D-mannose.

9. A process for preparing a radiolabelling kit according to claim 1, comprising the steps of:
   a) preparing or providing a solution comprising the suitable amount of acetate salt or buffer to balance at least the acidic pH eluate from a gallium-68 generator to a pH value between 3 to 5, preparing or providing the chelate-functionalized targeting agent and preparing or providing the metal inhibitor; and b) lyophilizing the solution obtained in step a).

10. A process for preparing a radiolabelling kit according to claim 1, comprising the steps of:

a) preparing or providing a solution comprising the chelate-functionalized targeting agent and the metal inhibitor;

b) lyophilizing the solution obtained in step a), and c1) adding the acetate salt as a powder in the obtained lyophilized product in step b), or c2) adding an acetate buffer in the obtained lyophilized product in step b).

11. A process for preparing a radiolabelling kit according to claim 1, comprising the steps of:

a) preparing a solution comprising the acetate salt, the chelate-functionalized targeting agent and the metal inhibitor; and b) optionally freeze the solution obtained in step a).

* * * * *